US012779137B2

(12) United States Patent
Tsoukalis

(10) Patent No.: US 12,779,137 B2
(45) Date of Patent: Nov. 3, 2026

(54) MINIATURE IV INFUSION LINE AIR ELIMINATOR

(71) Applicant: Micrel Medical Devices S.A., Koropi (GR)

(72) Inventor: Achilleas Tsoukalis, Papagou (GR)

(73) Assignee: Micrel Medical Devices S.A., Koropi (GR)

( * ) Notice: Subject to any disclaimer, the term of this patent is extended or adjusted under 35 U.S.C. 154(b) by 718 days.

(21) Appl. No.: 18/306,043

(22) Filed: Apr. 24, 2023

(65) Prior Publication Data

US 2023/0338670 A1 Oct. 26, 2023

(30) Foreign Application Priority Data

Apr. 22, 2022 (EP) .................................... 22169502

(51) Int. Cl.
*A61M 5/36* (2006.01)
*A61M 5/38* (2006.01)

(52) U.S. Cl.
CPC ............ *A61M 5/365* (2013.01); *A61M 5/385* (2013.01); *A61M 2205/7536* (2013.01)

(58) Field of Classification Search
CPC .......... A61M 5/36; A61M 5/365; A61M 5/38; A61M 5/385; A61M 2205/7536
See application file for complete search history.

(56) References Cited

U.S. PATENT DOCUMENTS 3,650,093 A 3/1972 Rosenberg
4,298,358 A * 11/1981 Ruschke ............... A61M 5/385 96/219
4,515,606 A * 5/1985 de Winter .......... B01D 19/0031 96/6
5,348,646 A * 9/1994 Costello, Jr. ........... B01D 61/18 210/94
6,251,292 B1 6/2001 Zuk
2004/0138616 A1* 7/2004 Guala ................ B01D 19/0031 604/122
2008/0264261 A1* 10/2008 Kavazov ............... A61M 5/165 96/219
2008/0269676 A1 10/2008 Bieberich et al.
(Continued)

FOREIGN PATENT DOCUMENTS

WO 2016191747 A1 12/2016

*Primary Examiner* — Devon C Kramer
*Assistant Examiner* — Henry Ng
(74) *Attorney, Agent, or Firm* — Bookoff McAndrews, PLLC

(57) ABSTRACT

Described is an infusion fluid air eliminating device comprising a body having a fluid passage region with a fluid inlet and a fluid outlet so as to define a fluid path from the fluid inlet to the fluid outlet, and a hydrophobic membrane, wherein the hydrophobic membrane covers the fluid passage region along a portion between the fluid inlet and the fluid outlet in a substantially sealed arrangement relative to the environment wherein there is provided a cavity on the side of the membrane facing the fluid passage region, and a pressurization unit is provided to pressurize the membrane against the fluid passage region such that the membrane essentially closes the cavity between the fluid inlet and the fluid outlet at one location when the pressure in the fluid is below a predetermined threshold value, and opens when the pressure in the fluid is not below the threshold value.

29 Claims, 6 Drawing Sheets

(56) References Cited

U.S. PATENT DOCUMENTS

| | | | | |
|---|---|---|---|---|
| 2010/0030151 | A1* | 2/2010 | Kirsch | A61M 5/36 604/126 |
| 2010/0222740 | A1* | 9/2010 | Park | A61M 5/44 604/114 |
| 2010/0270222 | A1* | 10/2010 | Lauer | A61M 5/385 210/205 |
| 2011/0066108 | A1* | 3/2011 | Geipel | A61M 5/16877 137/557 |
| 2011/0276010 | A1* | 11/2011 | Davis | A61M 39/20 604/257 |
| 2012/0234757 | A1* | 9/2012 | Martin | A61M 5/38 210/95 |
| 2013/0066272 | A1* | 3/2013 | Scagliarini | A61M 5/165 604/126 |
| 2014/0066849 | A1* | 3/2014 | Ki | A61M 5/445 604/114 |
| 2021/0046243 | A1* | 2/2021 | Guala | A61M 5/165 |
| 2021/0106745 | A1* | 4/2021 | Kashefi-Khorasani | A61M 1/3627 |
| 2021/0228856 | A1* | 7/2021 | Zafiris | A61M 39/24 |
| 2023/0253674 | A1* | 8/2023 | Kim | B62D 25/20 429/82 |
| 2024/0163357 | A1* | 5/2024 | Guo | H04M 1/0269 |

* cited by examiner

MINIATURE IV INFUSION LINE AIR ELIMINATOR

RELATED APPLICATIONS

This application claims priority to EP Patent Application No. 22169502.6, filed on Apr. 22, 2022, which is incorporated herein by reference in its entirety.

FIELD OF THE INVENTION

The present invention relates to an infusion fluid air eliminating device comprising a body having a fluid passage region with a fluid inlet and a fluid outlet so as to define a fluid path from the fluid inlet to the fluid outlet, and a hydrophobic membrane.

BACKGROUND OF THE INVENTION

Air in an intravenous infusion line can cause air embolism and death with patients receiving intravenous fluids through infusion pumps. In the prior art, infusion fluid air eliminating devices or, simply called, air eliminators are known as drip chambers or air eliminating filters. Drip chambers accumulate air in the top portion of a chamber where infusion drops come from, so that fluid in the bottom of the chamber is separated from air. Depression in the chamber which results from the weight of the fluid in the line and prohibits a free flow is maintained by the airtight structure of the drip chamber. In air eliminating filters, an airtight structure is divided in an upstream part and a downstream part by a first membrane being a hydrophilic membrane through which fluid but not air can pass, wherein the downstream part is filled with fluid, whereas air accumulated in the upstream part can escape by means of increased pressure in this part through an opening which is covered by a second membrane being a relatively small hydrophobic membrane, so that air bubbles are accumulating as they cannot go anywhere unless they find the relatively small hydrophobic membrane at the opposite side and are expelled out. This latter membrane lets air escape, but fluid cannot pass through. The size of such filters is large and the costs are high in case high infusion rates are required and more viscous drugs like parenteral nutrition are applied, because the hydrophilic membrane must have a large area to let the fluid pass through without excessively increasing the downstream pressure. Additionally, air eliminating filters eliminate also bacteria that cannot pass through the special hydrophilic membrane.

SUMMARY OF THE INVENTION

It is an object of the present invention to provide a novel infusion fluid air eliminating device with minimal size and costs and is therefore suitable to be easily integrated into an infusion cartridge such as disclosed e.g. in EP 3 017 836 A1 resulting in a minimal dimension infusion mechanism with an integrated air elimination function.

In order to overcome the above and further objects, according to a first aspect of the present invention, there is provided an infusion fluid air eliminating device comprising a body having a fluid passage region with a fluid inlet and a fluid outlet so as to define a fluid path from the fluid inlet to the fluid outlet, and a hydrophobic membrane, characterized in that the hydrophobic membrane covers the fluid passage region at least along a portion between the fluid inlet and the fluid outlet in a substantially sealed arrangement relative to the environment wherein there is provided a cavity on the side of the membrane facing the fluid passage region through which cavity fluid can pass from the fluid inlet under pressure to the fluid outlet, and a pressurization unit is provided to pressurize the membrane against the fluid passage region such that the membrane essentially closes the cavity between the fluid inlet and the fluid outlet at at least one location when the pressure in the fluid is below a predetermined threshold value, and opens when the pressure in the fluid is not below the threshold value, whereby air bubbles which may be contained in the fluid can escape from the cavity through the membrane, wherein preferably the predetermined threshold value corresponds to or is greater than the pressure to break the surface tension of the fluid.

The gist of the invention is the provision of a laminar flow exposing the fluid air mixture to a large area formed by the hydrophobic membrane. Whereas the flow in a tube has a cross-sectional area defined by the tube internal circle area, according to the present invention this area has been essentially enlarged to the area of the membrane. According to the present invention the air bubbles contained in the fluid are eliminated since they are enclosed in the cavity forming a thin section, and fluid is in pressure around, but the membrane where fluid cannot pass, but air can, is at lower atmospheric pressure. So, the air bubbles are exploding when they come in contact with the membrane, as the pressure is higher than their surface tension.

An important component for contributing the antisiphon effect according to the present invention is the pressurization unit which pressurizes the membrane against the fluid passage region such that the membrane substantially closes the cavity between the fluid inlet and the fluid outlet when the pressure in the fluid is below a predetermined threshold value being greater than the pressure to break the surface tension of the fluid, and opens when the pressure in the fluid is above the threshold value, whereby air bubbles which may be contained in the fluid can escape from the cavity through the membrane. Therefore a pressure needed for an antisiphon action higher than that for breaking surface tension can be provided.

The physics behind the present invention are that air under slightly higher pressure than the surrounding atmospheric pressure in contact with will escape through a hydrophobic membrane towards lower atmospheric pressure. So, to make it small so that it can be contained in an infusion mechanism cartridge, it does not need to have a hydrophilic membrane downstream as in air eliminating filters since the use of this large membrane for adult infusion rates results in increased dimensions.

According to the present invention as air can pass through the hydrophobic membrane, the air bubbles must be exposed as largely as possible to the large hydrophobic area of the membrane. This is done by the pump pressure that compresses the air bubbles and, hence, increases their pressure above surface tension. Air bubbles are accumulated to large air areas that even do not have surface tension as they are open from one side being large, since surface tension exists only in closed bubbles. So according to the present invention, there is provided a thin laminar flow of the fluid exposed from one side to the hydrophobic membrane while having means to slightly block the flow so as to increase the internal pressure above the surface tension of the fluid.

The operation of the pressurization unit to pressurize the membrane against the fluid passage region is advantageous not only for breaking the surface tension of the fluid but also for avoiding of a siphoning action, so that e.g. with the pump being arranged in a height of 1.5 m from the ground and away from a bed of the patient of 0.5 m height around 100 mbar under pressure must be retained in order to avoid siphoning. Since in this example 100 mbar is higher than the pressure to break the surface tension of all infusates used for intravenous infusions, both an antisiphon effect and an air elimination effect occurs. Preferably, the pressure from the pump and/or from the pressurizing unit should be above the working pressure in the infusion line, which is comparable to said 100 mbar, so that a pressure of 200 mbar as with most antisiphon valves available on the market is best.

As an example for the occurrence of an antisiphon action or effect, in case a tube is filled with fluid and its upper end is closed, the fluid stays in the tube irrespective of any movements of the tube; but if the upper end is opened, a siphoning action will occur wherein all fluid will drain irrespective of whether the tube curls and/or lifts and sinks.

So, the fluid passage region comprises a, preferably elongated, cavity which is provided on the side of the membrane facing the fluid passage region and communicates with the fluid inlet where forced intravenous fluid from an infusion pump enters the cavity at its upstream end, and with the fluid outlet at its downstream end where the fluid free from air enters the infusion line coupled to the fluid outlet.

The depth of the cavity is partly or in total small, comparable to smallest air bubbles.

The cavity is covered by the hydrophobic membrane which is fixed, e.g. by welding, to the portions of the body surrounding the cavity so that the cavity is closed towards the membrane for fluids, but open for air so that air bubbles can be expelled through the membrane out of the cavity and, hence, out of the fluid passage region due to internal pressure being higher than the atmospheric pressure.

So, the present invention provides means having an intrinsic flow restricting or antisiphon function, creating a pressure on the fluid being slightly higher than the atmospheric pressure to pass through the fluid passage region along the cavity from the fluid inlet to the fluid outlet.

Accordingly, after the fluid with air bubbles has entered the cavity, an antisiphon action increases the pressure in the fluid by means of infusion pump action, and the pressurized air bubbles come into contact with the hydrophobic membrane through which they are expelled out to the air wherein this phenomenon can be achieved in a particularly effective manner by having the depth of the cavity smaller than the diameter of the bubbles.

In the medical practice, the size of the air bubble even much bigger than a millimeter are usually not harmful for intravenous infusions. Preferably in practice air-in-line detectors are provided for calculation how much length of air with a given area of tube makes a volume of air per minute. Although a depth of the cavity being approximately 0.5 mm may be optimal for unifying air bubbles, a cavity having a depth being bigger or smaller might also be appropriate, wherein a range of the depth between 1 mm and 0.1 mm is preferably.

Preferred embodiments and modifications of the present invention are defined in the dependent claims.

Preferably the pressurization unit is adapted to pressurize against the fluid passage region the membrane on its side facing away from the fluid pas-sage region. In particular, the pressurization unit pressurizes the membrane from outside. However, in contrast to this preferred embodiment, the pressurization unit may alternatively be adapted to pressurize against the fluid passage region the membrane on its side facing towards the fluid passage region, i.e. from its inside, wherein the pressurization unit may be provided within the cavity and pulls the membrane against the fluid passage region.

According to a further preferred embodiment, the pressurization unit comprises at least one spring element so as to bias the membrane towards the fluid passage region. Most of air bubbles explode just before the spring element, whereas the cavity concentrates the smaller air bubbles to bigger ones.

According to a modification of the aforementioned preferred embodiment, the spring element extends substantially over the entire width of the fluid passage region transversely or angularly to the direction of flow of the fluid from the fluid inlet to the fluid outlet and preferably has an elongated shape. Such an arrangement renders the action of the spring element very effective.

According to a further modification, a plurality of spring elements are provided spaced from each other in the flow direction of the fluid from the fluid inlet to the fluid outlet.

According to a further modification, the spring element comprises a tube made of elastic material, preferably an elastomer tube.

According to an alternative modification, the spring element comprises sponge-like material. In particular, the spring element may comprise a sponge which is arranged above the membrane and pressurizes it so as to increase the pressure in the fluid while air passes through the sponge easily.

According to a further alternative modification, the spring element comprises a bent flat part which preferably comprises rubber-like material.

The sponge or rubber sheet can be compressed to a nominal antisiphon pressure by a cover. After all, pressure exercised on the membrane results in an antisiphon valve effect.

According to a still further alternative modification, a spring element is arranged in the area of the fluid outlet, wherein preferably such a spring element comprises a layer of elastic material, preferably of rubber-like material, which is stretched so as to pressurize the membrane against the fluid outlet.

If there is only one spring element, it has preferably to be placed just before the fluid outlet. If there are more, it is just the last or most downstream one that has to withstand the antisiphon pressure, whereas the others before need just to overcome the pressure to break surface tension.

In case a plurality of spring elements is provided, optionally all the spring elements can comprise the same construction according to one of the aforementioned alternative modifications, but it is also conceivable to provide spring elements having different constructions according to the aforementioned alternative modifications, e.g. to combine a spring element comprising sponge-like material or being formed as a sponge with a spring element comprising a bent flat part.

According to a further preferred embodiment, there is provided by a cover which is arranged on the body so as to cover the side of the membrane facing away from the fluid passage region and includes at least one air outlet opening. According to a modification of this embodiment, the spring element is arranged at least partly under pretension between the cover and the membrane, wherein preferably the pressurization unit is supported at least partly on the side of the cover facing the membrane.

According to a further preferred embodiment, the fluid passage region comprises a protrusion at at least one point between the fluid inlet and the fluid outlet, against which protrusion the membrane rests with its side facing the fluid passage region. The protrusion works as a flow obstacle, wherein the flow of the fluid is laminar along the membrane through a narrow gap between the hydrophobic membrane and the protrusion, so that air bubbles will be forced to come in contact with the membrane and expelled through the membrane out to the air. So, the fluid and air bubbles have to pass between the membrane and the obstacle whereby the membrane elevates slightly to generate a gap, which preferably is smaller than any air bubble, in a way that all air bubbles will come in contact with the membrane and will be eliminated.

According to a modification of the aforementioned embodiment, the protrusion extends substantially over the entire width of the fluid passage region transversely or angularly to the direction of flow of the fluid from the fluid inlet to the fluid outlet and preferably has an elongated shape. This construction allows a very effective function of the protrusion as a flow obstacle.

According to a further modification, a protrusion is arranged in the area of the fluid outlet or surrounds the fluid outlet so as to additionally provide an antisiphoning action. Preferably, the spring element may comprise a rubber sheet plate which compresses the membrane over a downstream portion of the fluid passage region having a surface which is elevated to the membrane height, so that the fluid cannot pass through if the pressure in the fluid is below the antisiphon pressure (free flow avoidance) but also air cannot come through and fill the outlet line coupled to the fluid outlet in case of an open infusion line end or a low line pressure (normal antisiphon action), since the rubber sheet covers all those parts. So, such rubber sheet plate causes an antisiphon effect. In addition, that part of membrane under the rubber sheet plate can be painted with a sealing air sealant. This sealing of the membrane can be done on and after the last downstream spring element to assure an antisiphon action.

According to a further modification, at least three protrusions are provided spaced apart from each other in the direction of flow of the fluid from the fluid inlet to the fluid outlet, thereby dividing the cavity into at least two cavity sections. So, the cavity sections are able to concentrate smaller air bubbles to bigger ones step by step, wherein the membrane bends above to allow the fluid pass over the protrusions through the cavity sections from the fluid inlet to the fluid outlet. In this case, if a cover is provided, it preferably includes at least two air discharge openings, one air discharge opening being in communication with the one cavity section and the other air discharge opening being in communication with another cavity section.

There may be several smaller or zero depth protrusions in the flow, forcing the fluid to lift the membrane and, hence, to push it higher to have space to pass through, and so forcing air bubbles out. After passing over a number of obstacles, the fluid is free from air bubbles to exit into the fluid outlet.

According to a further modification, at least one spring element is arranged over a protrusion so that it pressurizes the membrane against the protrusion. So, the membrane is sandwiched between a spring element and a protrusion which results in rendering the function of each the spring element and the protrusion very effective. So, the function of the spring element as a flow restrictor is enhanced by biasing the membrane from above upon a protrusion working as an obstacle, wherein preferably the spring element extends along the protrusion transverse to the flow.

According to a further preferred embodiment, the fluid passage region comprises a recess having an outwardly open side covered by the membrane, whereby the recess forms the cavity. This construction allows a very simple provision of the cavity under the membrane.

According to a modification of the above preferred embodiment, the body has a substantially planar surface into which the recess is incorporated and to which the membrane is attached in a substantially sealed arrangement relative to the environment.

According to a further modification, the recess comprises a bottom on which the protrusion is arranged, wherein preferably the protrusion terminates in the plane spanned by the surface.

According to a further modification, the recess is bounded by two spaced side walls extending in the direction of flow of the fluid from the fluid inlet to the fluid outlet, and the protrusion is adjacent to at least any one of the two side walls.

According to a further modification, the protrusion arranged in the area of the fluid outlet and/or surrounding the fluid outlet is adjacent to the downstream end of the recess with respect to the direction of flow of the fluid from the fluid inlet to the fluid outlet or is arranged outside and downstream of the recess.

In addition, a flow restrictor or an antisiphon unit within the device or downstream of it may increase the working pressure in the fluid passage region of the infusion fluid air eliminating device. So, the antisiphon action may be enforced by the provision of an external antisiphon unit in the infusion line increasing working pressure in the fluid.

According to a further aspect of the present invention, there is provided an infusion pump mechanisms cartridge which comprises an infusion fluid air eliminating device according to the first aspect. Namely, the infusion fluid air eliminating device according to the first aspect can be easily integrated into an infusion cartridge such as disclosed e.g. in EP 3 017 836 A1 resulting in a minimal dimension infusion mechanism with an integrated air elimination function. Air in line detectors are provided to check if substantial air above a certain limit is passing into the line, and without elimination of the air unwanted alarms are frequent. The infusion fluid air eliminating device according to the first aspect can be integrated into the infusion segment of a pump before an air-in-line detector so as to reduce possible unwanted alarms. For best false alarm avoidance, there may be provided two air in line detectors, one upstream the infusion fluid air eliminating device detecting if the reservoir is empty and therefore a lot of air is present, and one downstream the infusion fluid air eliminating device to verify that air is absent and in the unlikely event the occurrence of an alarm for air in line results from a real problem in the membrane or other parts.

DESCRIPTION OF A PREFERRED EMBODIMENT

FIGS. 1 to 7 show an infusion fluid air eliminating device 2 according to a preferred first embodiment comprising a body 10 which is rectangular- or cube-shaped and, hence, has a planar surface 10*a*. The body 10 is provided at its one narrow end portion with a fluid inlet 12 and at its opposite other narrow end portion with a fluid outlet 14. In the embodiment shown, both the fluid inlet 12 and fluid outlet 14 are embodied as through holes.

Figure 6:
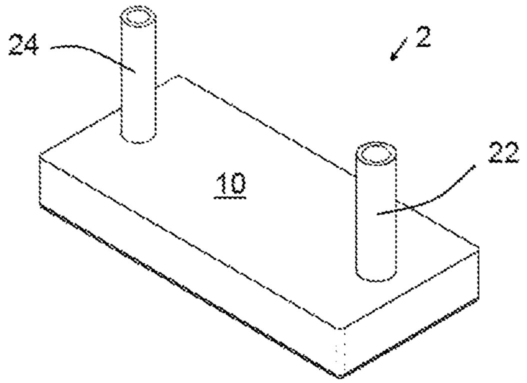
FIG. 6 shows a perspective view of the device of FIG. 5 from below.
Figure 1:
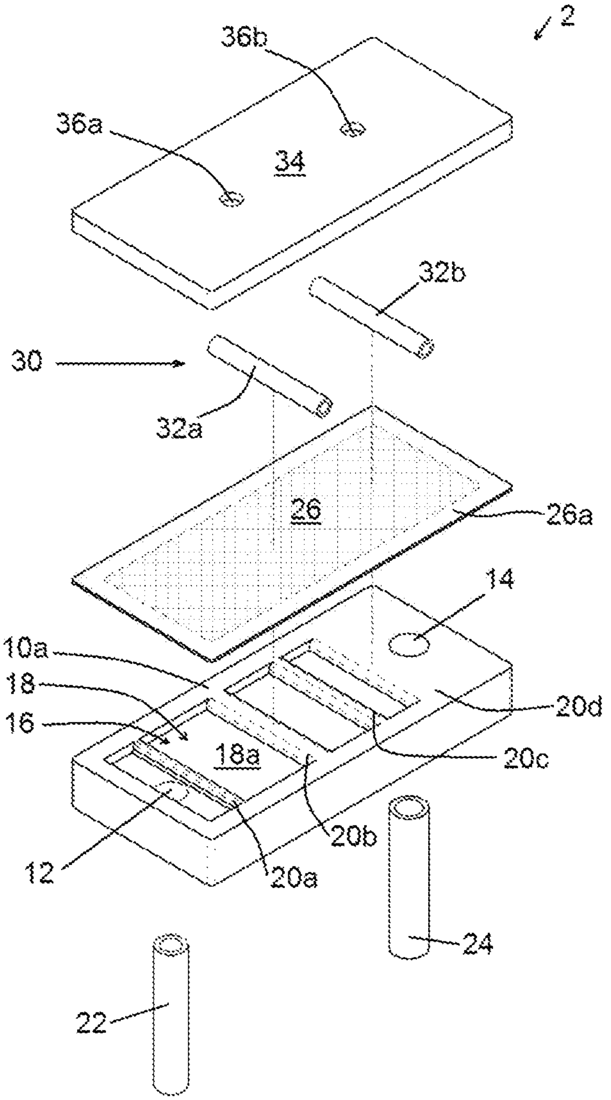
FIG. 1 shows an infusion fluid air eliminating device according to a preferred first embodiment in an exploded view.
Figure 2:
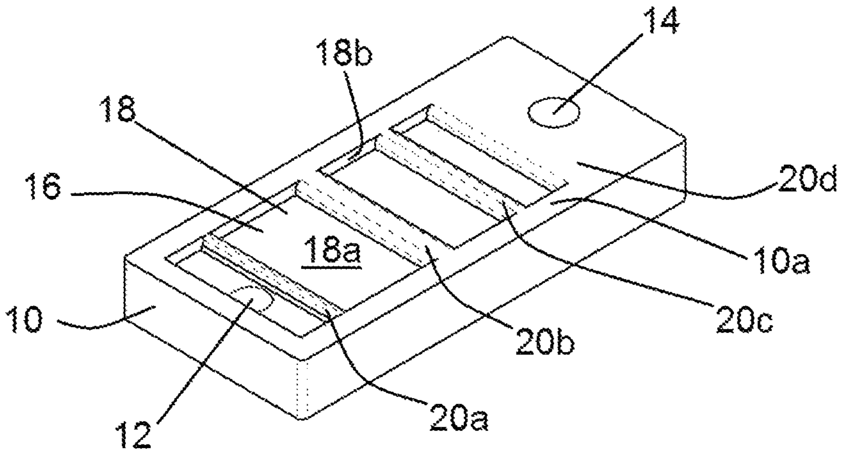
FIG. 2 shows a perspective view of the body of the device of FIG. 1 from above.
Figure 3:
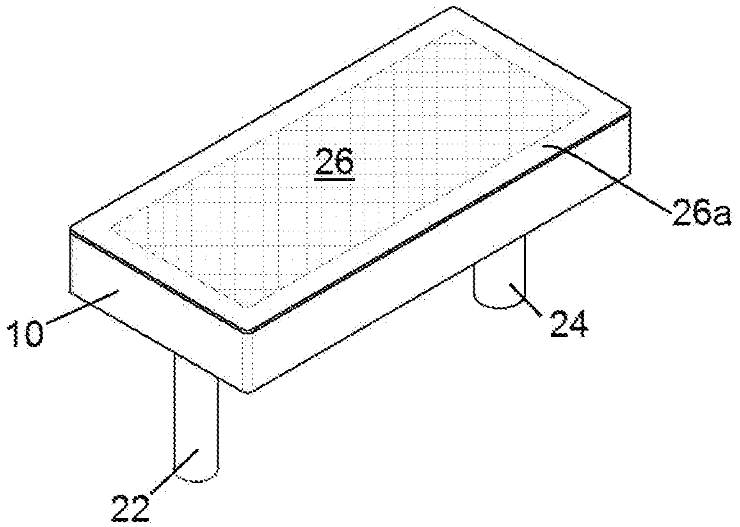
FIG. 3 shows a perspective view of the body of FIG. 2 along with a portion of a fluid inlet tube and a portion of a fluid outlet tube as well as a membrane arranged on the body.

The body comprises a fluid passage region 16 which defines a fluid path from the fluid inlet 12 to fluid outlet 14 and includes a recess 18 having an outwardly open side which faces the viewer of the FIGS. 1 and 2. The recess 18 has a rectangular shape, comprises a bottom 18*a* and is bounded by four sidewalls including two spaced short sidewalls extending transversely to the longitudinal extension of the body 10 and two spaced long sidewalls 18*b* extending in the direction of the longitudinal extension of the body 10 and, hence of the flow path from the fluid inlet 12 to fluid outlet 14, wherein one of both the long sidewalls 18*b* is visible in FIG. 2. In the embodiment shown, the bottom 18*a* of the recess 18 is arranged in parallel to the plane spanned by the planar surface 10*a* of the body 10 so that the sidewalls of the recess 18 have the same height and, hence, the depth of the recess 18 is at each point the same. As described above and to be shown from the FIGS. 1, 2 and 7, the recess 18 forms a cavity.

Figure 7:
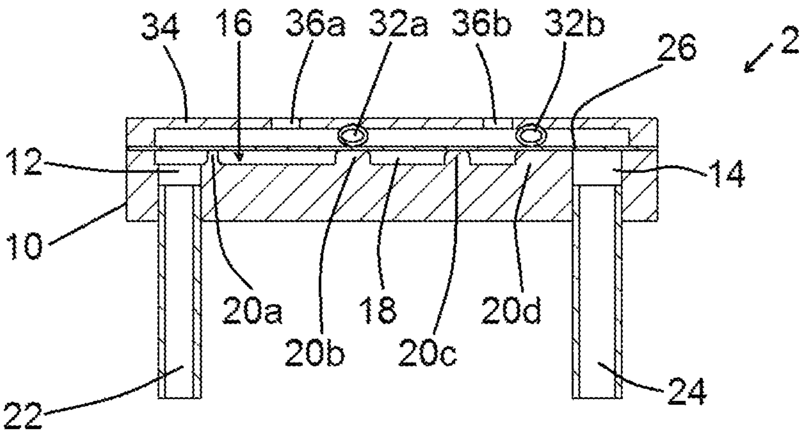
FIG. 7 shows a longitudinal section through the device of FIG. 5 from the fluid inlet to the fluid outlet.

As further shown in FIGS. 1, 2 and 7, the body 10 comprises four protrusions 20*a*, 20*b*, 20*c* and 20*d* which are spaced apart from each other in the direction of the longitudinal extension of the body 10 and, hence, in the direction of flow of the fluid from fluid inlet 12 to fluid outlet 14, thereby dividing the recess 18 into four cavity sections. The protrusions 20*a*, 20*b* and 20*c* each have an elongated shape extending transversely to the longitudinal extension of the body 10. The protrusions 20*a*, 20*b* and 20*c* are arranged on the bottom 18*a* of the recess 18 and terminates in the plane spend by the planar surface 10*a* of the body 10. Moreover, as shown in FIGS. 1 and 2, the elongated protrusions 20*a*, 20*b* and 20*c* each extend over the whole width of the recess 18 so as to join at their ends both the long sidewalls 18*b*. In the embodiment shown, the most downstream fourth protrusion 20*d* is defined by a portion of the downstream portion of the planar surface 10*a* of the body 10 which portion includes the fluid outlet 14 so that the fourth protrusion 20*d* surrounds the fluid outlet 14 as shown in the FIGS. 1, 2 and 7. At the same time, the fourth protrusion 20*d* defines the downstream border of the recess 18 by forming the downstream short sidewall so that the fourth protrusion 20*d* is adjacent to the downstream end of the recess 18 with respect to the longitudinal extension of the body 10 and, hence, of the flow of the fluid from fluid inlet 12 to fluid outlet 14.

As shown in the FIGS. 1 and 3 to 7, a fluid inlet tube 22 is to be coupled to the fluid inlet 12 and a fluid outlet tube 24 is to be coupled to the fluid outlet 14 wherein in the given figures only portions of the tubes 22 and 24 are depicted. As further shown in these figures, the tubes 22 and 24 are arranged at the backside of the body 10 opposite to its planar surface 10*a*.

As shown in the FIGS. 1, 3, 4 and 7, the planar surface 10*a* of the body 10 is covered by a membrane 26 which is a hydrophobic membrane and, hence, is able to let air pass through, but to hold fluid back. In the embodiment shown, the membrane 26 has essentially the same shape as the planar surface 10*a* of the body and is only fixed with his surrounding edge portion 26*a* to the corresponding surrounding edge portion of the planar surface 10*a* in a sealed arrangement relative to the environment, in particular by welding. Thus, the membrane 26 loosely lies upon all the protrusions 20*a* to 20*d*, so that by lifting the membrane 26 a small gap appears between the top of the protrusions 20*a* to 20*d* and the inner side of the membrane facing the recess 18 so as to allow the fluid to flow from the fluid inlet 12 over the protrusions 20*a* to 20*d* to the fluid outlet 14, wherein in particular along the top of the fourth protrusion 20*d* a fluid path occurs from the recess 18 to the fluid outlet 14.

Figure 4:
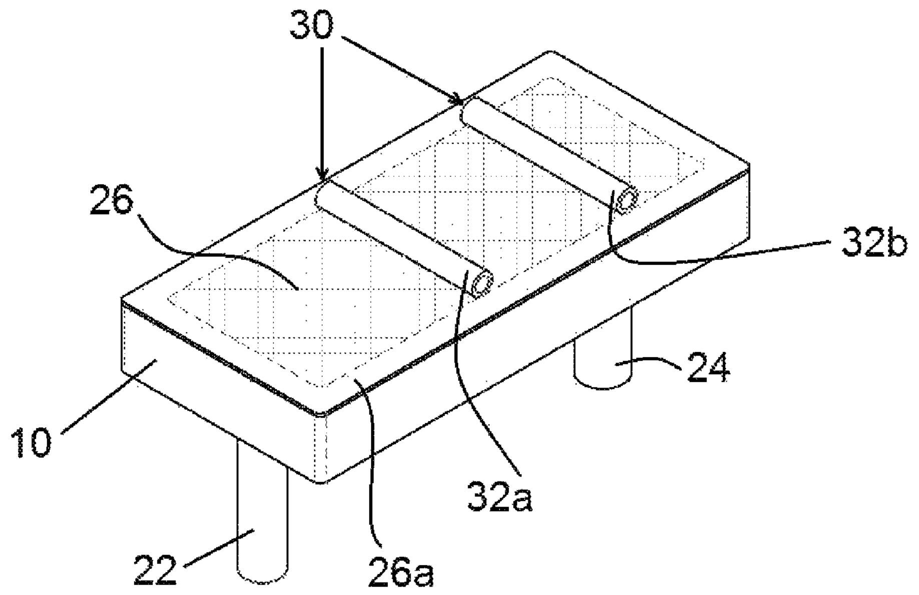
FIG. 4 shows the same arrangement as FIG. 3, but with additionally elastomeric tubes as spring elements arranged upon the exterior of the membrane.

As further to been seen from the FIGS. 1, 4 and 7, there is provided a pressurization unit 30. The function of this unit 30 is to pressurize and, hence, to bias the membrane 26 against the fluid passage region 16 and its recess 18 so that the membrane 26 comes in contact with the top of the protrusions 20*a* to 20*d* with the result that the flow path between the fluid inlet 12 and the fluid outlet 14 can be blocked. However, this is only the case when the pressure in the fluid is below a predetermined threshold value which corresponds or is greater than the pressure to break the surface tension of the fluid. However, the pressurization unit 30 is adapted to generate a pressure having a value which is below said predetermined threshold so that the membrane 26 is lifted by the pressure in the fluid in case the pressure in the fluid is above said predetermined threshold value. In the embodiment shown, the pressurization unit 30 is arranged at the side of the membrane 26 facing away from the recess 18 and, hence, at the exterior of the membrane 26.

Preferably, the pressurization unit 30 comprises at least one spring element 32*a*, 32*b* which extends substantially over the entire width of the fluid passage region 16 or the recess 18 or the membrane 26 transversely or angularly to the longitudinal extension of the body 10 and, hence, to the direction of flow of the fluid from the fluid inlet 12 to the fluid outlet 14. Although preferably, a plurality of such spring elements 32*a*, 32*b* are provided spaced from each other in the longitudinal extension of the body 10 and, hence, in the flow direction of the fluid from the fluid inlet 12 to fluid outlet 14. It is further preferred that a spring element is arranged over a protrusion (e.g. 20*b*, 20*d*) so that it pressurizes the membrane 26 against such protrusion.

According to the first preferred embodiment of the device 2, there are two spaced spring elements 32*a*, 32*b* which each have an elongated shape and are provided as a tube made of elastic material, preferably an elastomer tube.

Figure 5:
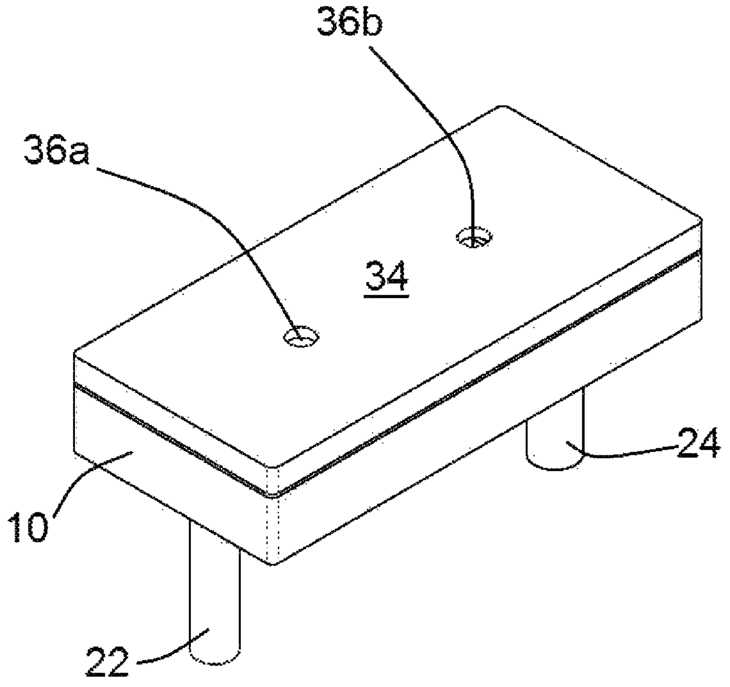
FIG. 5 shows a perspective view of the arrangement of FIG. 4 upon which a cover is additionally arranged, and hence the whole assembly of the infusion fluid air eliminating device according to the preferred first embodiment.

As further shown in the FIGS. 1, 5 and 7, a cover 34 is provided which is arranged on the body 10 so as to cover the side of the membrane 26 facing away from the fluid passage region 16 and the recess 18 and, hence, the exterior of the membrane 26 and also to cover the pressurization unit 30. The cover 34 is formed such that at its inner side facing the membrane 26 there is provided a space which accommodates the spring elements 32*a*, 32*b* of the pressurization unit 30, as to be seen from FIG. 7. The depth of such space is dimensioned such that the spring element 32*a*, 32*b* of the pressurization unit 30 are supported on the inner side of the cover 34 and further arranged under pretention between the cover 34 and the membrane 26.

In the embodiment shown, the cover 34 includes two air discharge openings 36*a*, 36*b*, wherein the air discharge opening 36*a* is in communication with the one cavity section being the second cavity section in the order of cavity sections from the fluid inlet 12 to fluid outlet 14 and with the other air discharge opening 36*b* being in communication with the most downstream fourth cavity section, as in particular it becomes clear from FIG. 7.

Figure 8:
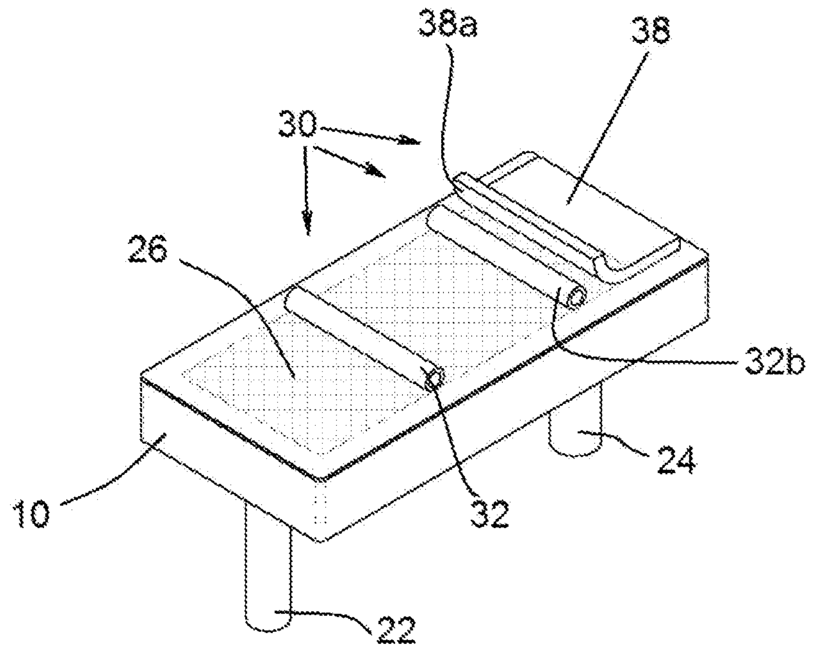
FIG. 8 shows, similar to FIG. 4, an arrangement of the body, the membrane and the pressurizing unit of an infusion fluid air eliminating device according to a preferred second embodiment.
Figure 9:
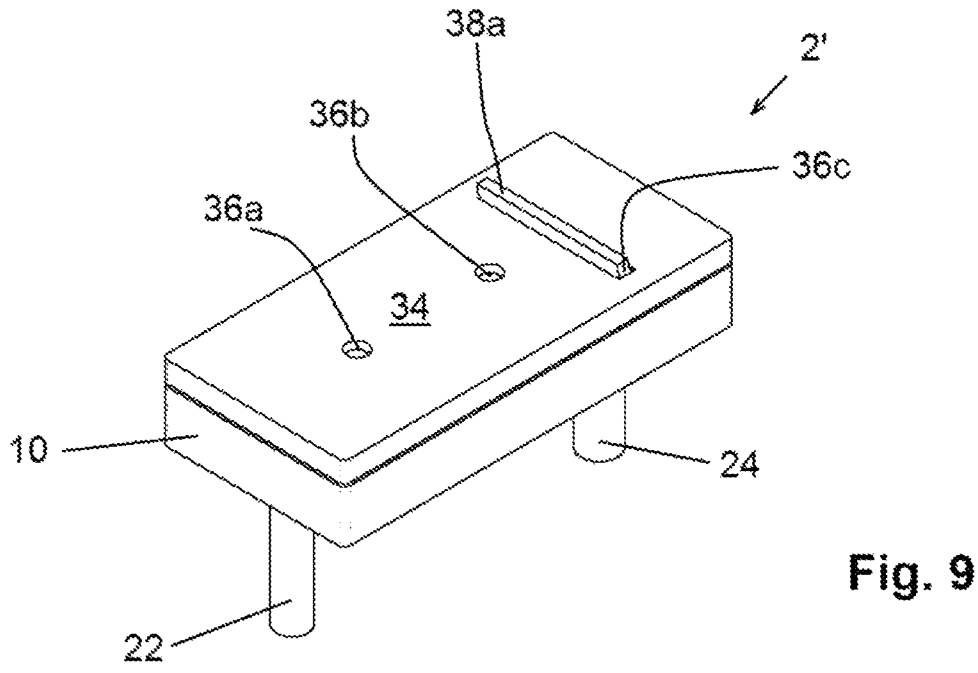
FIG. 9 shows, similar to FIG. 5, the whole assembly of the device according the preferred second embodiment.
Figure 10:
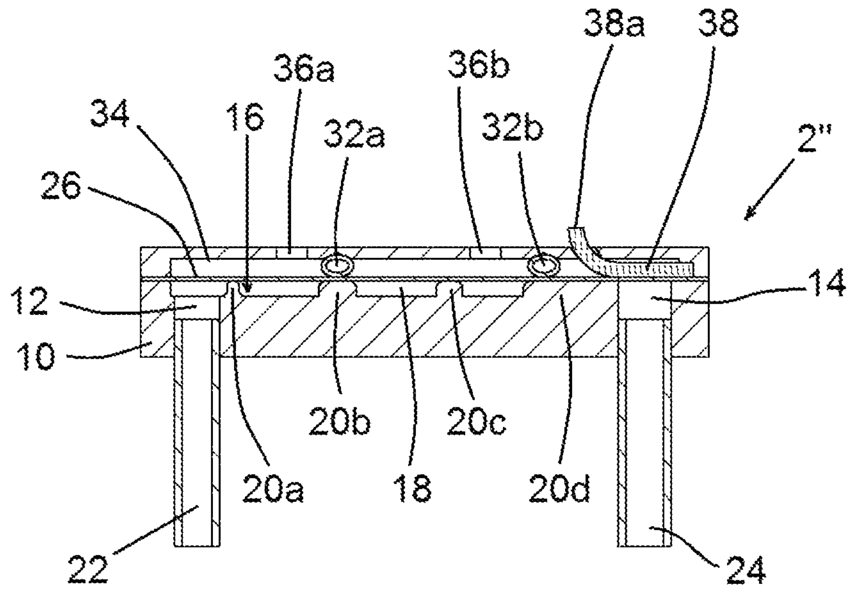
FIG. 10. shows a longitudinal section through the device of FIG. 9.

In FIGS. 8 to 10 it is shown an infusion fluid air eliminating device 2' according to a preferred second embodiment which differs from the above described preferred first embodiment in that the pressurization unit 30 comprises in addition to the tube-formed spring elements 32*a*, 32*b* a bent flat part 38 as a further spring element which is arranged upon the membrane 26 in the area of the fluid outlet 14 so that in that area the membrane 26 is sandwiched between the bent flat part 38 and the fourth protrusion 20*d*. The bent flat part 38 is preferably made of rubber-like material. As further shown in the FIGS. 8 to 10, the bent flat part is curved above and comprises a free end 38*a* facing upwards through a slit-shaped opening 36*c* which is additionally included in the cover 34.

Figure 11:
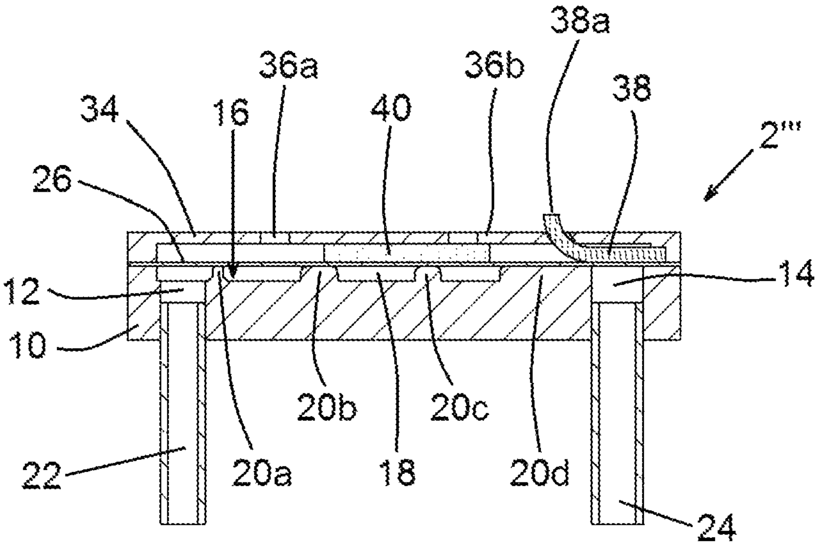
FIG. 11 shows a longitudinal section through an infusion fluid air eliminating device according to a preferred third embodiment.

Moreover, FIG. 11 shows a longitudinal section through a device 2" according to a preferred third embodiment which differs from the second embodiment of the FIGS. 8 to 10 that instead of the spring elements 32*a*, 32*b* a flat sponge 40 is provided so that the pressurization unit 30 of the preferred third embodiment comprises the bent flat part 38 and the sponge 40.

With respect thereto, it should be added that in alternative embodiments not shown here the pressurization unit 30 can comprise only the bent flat part 38 or the sponge 40.

Figure 12:
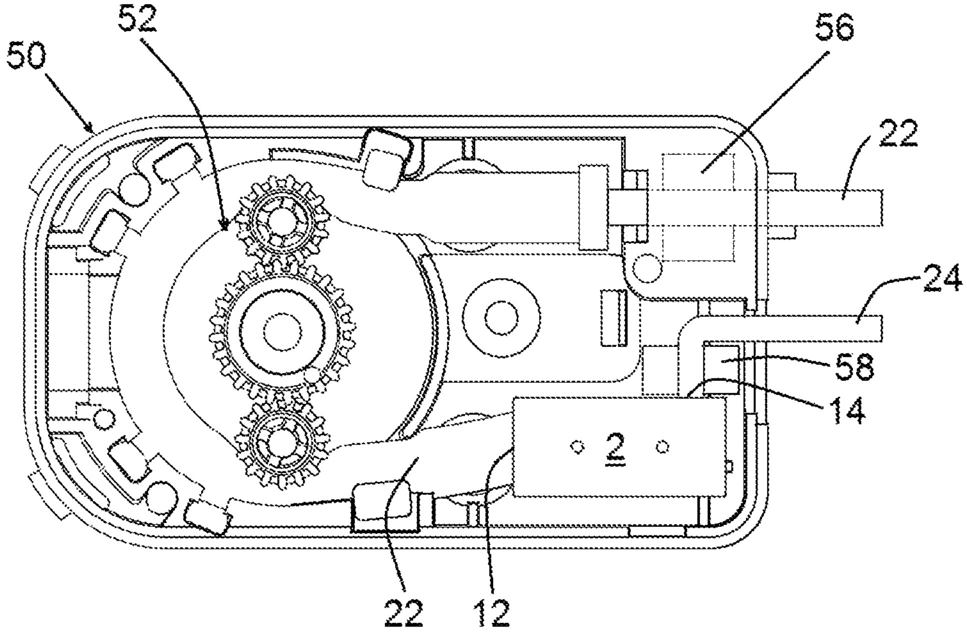
FIG. 12 shows the interior of an infusion pump mechanism cartridge according to a preferred embodiment including the infusion fluid air eliminating device.

The infusion fluid air eliminating device 2 as described above can be easily integrated into an infusion pump mechanisms cartridge 50 including a pump mechanism 52 as exemplarily shown in FIG. 12 (which also applies to the device 2' or 2" according to the second and third embodiments as described above). For a convenient false alarm avoidance, the infusion pump mechanisms cartridge 50 further includes two air-in-line detectors 56, 58, which both are preferably ultrasonic sensors, wherein a first sensor 56 is provided upstream of the fluid inlet 12 of the device 2 so as to detect air bubbles in the fluid inlet tube 22, and a second sensor 58 is provided downstream of the fluid outlet 14 of the device 2 so as to detect possible air bubbles in the fluid outlet tube 24.

Intravenous fluid from an infusion pump enters the cavity formed by the recess 18 at its upstream end through the fluid inlet 12, and the fluid free from air leaves the fluid path fluid at its downstream end through the fluid outlet 14 so as to enter the fluid outlet line 24.

The depth of said cavity is preferably narrow in full or in parts like the spring elements 32*a*, 32*b*, comparable to smallest air bubbles.

There are means having an intrinsic antisiphon function like the spring elements 32*a*, 32*b* creating a pressure slightly higher than atmospheric pressure on the fluid to let it pass through the cavity to the downstream fluid outlet 14.

The recess 18 has one side covered by a sealed hydrophobic membrane 26 along all four recess borders so that for fluids it defines a closed cavity, but for air an open one, and an internal pressure higher than atmospheric pressure expels air bubbles out. Accordingly, after the fluid with air bubbles has entered the recess 18, an antisiphon action increases the pressure in the fluid by means of infusion pump action, and the pressurized air bubbles come into contact with the hydrophobic membrane 26 through which they are expelled out to the air wherein this phenomenon can be achieved in a particularly effective manner by having the depth of the cavity 26 smaller than the diameter of the bubbles. The recess 18 acts also as a collider of small air bubbles to bigger ones, until they become big enough to explode on the membrane 26.

There may be several smaller or zero depth protrusions 20*a* to 20*d* in the flow path, forcing the fluid to lift the membrane 26 and, hence, to push it higher to have space to pass through, and so forcing air bubbles out. After passing over the plurality of protrusions 20*a* to 20*d*, the fluid is free from air bubbles to exit into the fluid outlet 14.

An antisiphon action may be additionally enforced by the provision of an external antisiphon unit (not shown) in the infusion line increasing working pressure in the fluid.

An important component for contributing the antisiphon effect is the pressurization unit 30 which pressurizes the membrane 26 against the fluid passage region 16 such that the membrane 26 substantially closes the cavity forming recess 18 between the fluid inlet 12 and the fluid outlet 14 when the pressure in the fluid is below a predetermined threshold value corresponding to or being greater than the pressure to break the surface tension of the fluid, and opens when the pressure in the fluid is above the threshold value, whereby air bubbles which may be contained in the fluid can escape from the cavity 18 through the membrane 26.

Preferably, the pressurization unit 30 comprises at least one spring element. According to a modification, the spring element comprises a flow restrictor, like an elastomeric tube 32*a*, 32*b*, to be biased from above upon the membrane 26 over a protrusion 20*b*, 20*d* and preferably extends along the protrusion 20*b*, 20*d* transverse to the flow, wherein the most downstream protrusion 20*d* is provided in the area of the fluid outlet 14. At the protrusions 20*b*, 20*d*, fluid and air bubbles will have to pass between the membrane 26 and the protrusions 20*b*, 20*d* whereby the membrane 26 elevates slightly to generate a gap, which preferably is smaller than any air bubble, in a way that all air bubbles come in contact with the membrane 26 and are eliminated.

According to a further embodiment of FIG. 11, the spring element may comprise a sponge 40 which is arranged above the membrane 26 and presses it in contact with the protrusions 20*b*, 20*c* so as to increase the pressure in the fluid while air passes through the sponge easily. According to a further modification as shown in the FIGS. 8 to 11, the spring element may comprise a rubber sheet plate 38 which compresses the membrane 26 over a downstream portion of the fluid passage region having a surface which is elevated towards the membrane 26 so that the fluid cannot pass through if the pressure in the fluid is below the antisiphon pressure (free flow avoidance) but also air cannot come through and fill the fluid path in case of an open infusion line end or a low line pressure (normal antisiphon action), since the rubber sheet plate 38 covers all those parts. So, the rubber sheet plate 38 causes an antisiphon effect. In addition, that part of the membrane 26 under the rubber sheet plate 38 can be paint with a sealing air sealant. The sponge 40 and/or the rubber sheet plate 38 can be compressed to a nominal antisiphon pressure by the cover 34. After all, the pressure exercised on the membrane 26 results in an antisiphon valve effect.

The invention claimed is:

1. An infusion fluid air eliminating device comprising a body having a fluid passage region with a fluid inlet and a fluid outlet so as to define a fluid path from the fluid inlet to the fluid outlet, and a hydrophobic membrane, characterized in that:

the hydrophobic membrane covers the fluid passage region at least along a portion between the fluid inlet and the fluid outlet in a substantially sealed arrangement relative to the environment wherein there is provided a cavity on the side of the hydrophobic membrane facing the fluid passage region through which cavity fluid can pass from the fluid inlet under pressure to the fluid outlet, and a pressurization unit is provided to pressurize the hydrophobic membrane against the fluid passage region such that the hydrophobic membrane essentially closes the cavity between the fluid inlet and the fluid outlet at at least one location when the pressure in the cavity fluid is below a predetermined threshold value, and opens when the pressure in the cavity fluid is not below the predetermined threshold value, whereby air bubbles which may be contained in the cavity fluid can escape from the cavity through the hydrophobic membrane, wherein the predetermined threshold value corresponds to or is greater than the pressure to break the surface tension of the cavity fluid.

2. The infusion fluid air eliminating device according to claim 1, wherein the pressurization unit is adapted to pressurize against the fluid passage region the hydrophobic membrane on its side facing away from the fluid passage region.

3. The infusion fluid air eliminating device according to claim 1, wherein the pressurization unit comprises at least one spring element.

4. The infusion fluid air eliminating device according to claim 3, wherein the at least one spring element extends substantially over the entire width of the fluid passage region transversely or angularly to the direction of flow of the cavity fluid from the fluid inlet to the fluid outlet, and further wherein the at least one spring element has an elongated shape.

5. The infusion fluid air eliminating device according to claim 3, wherein the at least one spring element is a plurality of spring elements and the plurality of spring elements are spaced from each other in the flow direction of the cavity fluid from the fluid inlet to the fluid outlet.

6. The infusion fluid air eliminating device according to claim 5, wherein sealing of the hydrophobic membrane is done on and after the last downstream spring element of the at least one spring element to assure an antisiphon action.

7. The infusion fluid air eliminating device according to claim 3, wherein the at least one spring element comprises a tube made of elastic material.

8. The infusion fluid air eliminating device according to claim 3, wherein the at least one spring element comprises a sponge-like material.

9. The infusion fluid air eliminating device according to claim 3, wherein the at least one spring element comprises a bent flat part.

10. The infusion fluid air eliminating device according to claim 3, wherein the at least one spring element is arranged in an area of the fluid outlet.

11. The infusion fluid air eliminating device according to claim 10, wherein the at least one spring element comprises a layer of elastic material and the elastic material is stretched so as to pressurize the hydrophobic membrane against the fluid outlet.

12. The infusion fluid air eliminating device according to claim 3, further comprising a cover arranged on the body so as to cover the side of the hydrophobic membrane facing away from the fluid passage region.

13. The infusion fluid air eliminating device according to claim 12, wherein the cover includes at least one air outlet opening.

14. The infusion fluid air eliminating device according to claim 12, wherein the at least one spring element is arranged at least partly under pretension between the cover and the hydrophobic membrane.

15. The infusion fluid air eliminating device according to claim 14, characterized in that the pressurization unit is supported at least partly on the side of the cover facing the hydrophobic membrane.

16. The infusion fluid air eliminating device according to claim 12, wherein the cover includes at least two air discharge openings, a first air discharge opening being in communication with a first section of the cavity and a second air discharge opening being in communication with a second section of the cavity.

17. The infusion fluid air eliminating device according to claim 1, wherein the fluid passage region comprises a protrusion at at least one point between the fluid inlet and the fluid outlet, against which the hydrophobic membrane rests with its side facing the fluid passage region.

18. The infusion fluid air eliminating device according to claim 17, wherein the protrusion extends substantially over the entire width of the fluid passage region transversely or angularly to the direction of flow of the cavity fluid from the fluid inlet to the fluid outlet.

19. The infusion fluid air eliminating device according to claim 17, wherein the protrusion is arranged in an area of the fluid outlet or surrounds the fluid outlet.

20. The infusion fluid air eliminating device according to claim 17, wherein the protrusion comprises at least three protrusions, wherein the at least three protrusions are spaced apart from each other in the direction of flow of the cavity fluid from the fluid inlet to the fluid outlet, thereby dividing the cavity into at least two cavity sections.

21. The infusion fluid air eliminating device according to claim 17, wherein at least one spring element is arranged over the protrusion so that it pressurizes the hydrophobic membrane against the protrusion.

22. The infusion fluid air eliminating device according to claim 17, wherein the fluid passage region comprises a recess having an outwardly open side covered by the hydrophobic membrane, whereby the recess forms the cavity.

23. The infusion fluid air eliminating device according to claim 22, wherein the body has a substantially planar surface into which the recess is incorporated and to which the hydrophobic membrane is attached in a substantially sealed arrangement relative to the environment.

24. The infusion fluid air eliminating device according to claim 23, wherein the protrusion terminates in a plane spanned by the substantially planar surface.

25. The infusion fluid air eliminating device according to claim 22, wherein the recess comprises a bottom on which the protrusion is arranged.

26. The infusion fluid air eliminating device according to claim 22, wherein the recess is bounded by two spaced side walls extending in the direction of flow of the cavity fluid from the fluid inlet to the fluid outlet, and the protrusion is adjacent to at least any one of the two spaced side walls.

27. The infusion fluid air eliminating device according to claim 22, wherein the protrusion arranged in an area of the fluid outlet and/or surrounding the fluid outlet is adjacent to the downstream end of the recess with respect to the direction of flow of the cavity fluid from the fluid inlet to the fluid outlet or is arranged outside and downstream of the recess.

28. An infusion pump mechanism cartridge comprising an infusion fluid air eliminating device, the device comprising a body having a fluid passage region with a fluid inlet and a fluid outlet so as to define a fluid path from the fluid inlet to the fluid outlet, and a hydrophobic membrane, the hydrophobic membrane covers the fluid passage region at least along a portion between the fluid inlet and the fluid outlet in a substantially sealed arrangement relative to the environment wherein there is provided a cavity on the side of the hydrophobic membrane facing the fluid passage region through which cavity fluid can pass from the fluid inlet under pressure to the fluid outlet, and a pressurization unit is provided to pressurize the hydrophobic membrane against the fluid passage region such that the hydrophobic membrane essentially closes the cavity between the fluid inlet and the fluid outlet at at least one location when the pressure in the cavity fluid is below a predetermined threshold value, and opens when the pressure in the cavity fluid is not below the predetermined threshold value, whereby air bubbles which may be contained in the cavity fluid can escape from the cavity through the hydrophobic membrane, wherein the predetermined threshold value corresponds to or is greater than the pressure to break the surface tension of the cavity fluid.

29. The infusion pump mechanism cartridge according to claim 28, further comprising a first air sensor provided upstream of the fluid inlet and a second air sensor provided downstream of the fluid outlet.

* * * * *